United States Patent [19]

Welch et al.

[11] 4,352,807

[45] Oct. 5, 1982

[54] HEXAHYDRO-TRANS-PYRIDOINDOLE NEUROLEPTIC AGENTS

[75] Inventors: Willard M. Welch, Mystic; Charles A. Harbert, Waterford, both of Conn.

[73] Assignee: Pfizer Inc., New York, N.Y.

[21] Appl. No.: 182,177

[22] Filed: Aug. 28, 1980

Related U.S. Application Data

[62] Division of Ser. No. 61,573, Jul. 30, 1979, Pat. No. 4,252,811.

[51] Int. Cl.$^3$ ............... C07D 471/14; A61K 31/445
[52] U.S. Cl. ................................. 424/256; 546/85; 546/86
[58] Field of Search ................ 546/85, 86; 424/256

[56] References Cited

U.S. PATENT DOCUMENTS

| | | | |
|---|---|---|---|
| 3,687,961 | 8/1972 | Bernstein | 546/85 |
| 3,983,239 | 9/1976 | Nagai et al. | 424/267 |
| 3,991,199 | 11/1976 | Berger | 424/267 |
| 4,001,263 | 1/1977 | Plattner et al. | 546/85 |
| 4,141,980 | 2/1979 | Berger | 424/256 |

*Primary Examiner*—Alan L. Rotman
*Attorney, Agent, or Firm*—Charles J. Knuth; Albert E. Frost; Robert K. Blackwood

[57] ABSTRACT

Medicinal agents classed as 2-(aminoalkyl or amidoalkyl)-5-aryl-hexahydro-trans-4a,9b-1(H)-pyrido-[4,3-b]indole derivatives have been synthesized and found to have neuroleptic activity.

15 Claims, No Drawings

HEXAHYDRO-TRANS-PYRIDOINDOLE NEUROLEPTIC AGENTS

CROSS REFERENCE TO RELATED APPLICATION

This application is a division of pending application Ser. No. 061,573 filed July 30, 1979, now U.S. Pat. No. 4,252,811, issued Feb. 24, 1981.

BACKGROUND

The successful treatment of schizophrenic behavior using antipsychotic tranquilizers such as chlorpromazine has stimulated research to find other neuroleptic agents having improved biological profiles. One such class of compounds is the hexahydropyrido[4,3-b]indoles. The basic ring structure is

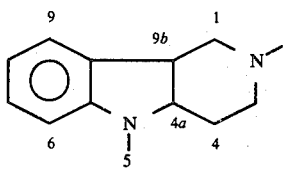

and the stereochemistry at positions 4a and 9b may be cis or trans. Examples of hexahydropyridoindoles that are useful as tranquilizers, neuroleptic agents, analgesics, sedatives, muscle relaxants and hypotensive agents are given in the following U.S. patents: U.S. Pat. No. 3,687,961; U.S. Pat. No. 3,983,239; U.S. Pat. No. 3,991,199; U.S. Pat. No. 4,001,263 and U.S. Pat. No. 4,141,980.

It has now been discovered that novel hexahydro-trans-4a,9b-pyrido[4,3-b]indoles substituted at the 5 position with an aryl group and the 2 position with an aminoalkyl group or an amidoalkyl group exhibit potent neuroleptic activity.

SUMMARY

The neuroleptic agents of the present invention are (+) enantiomeric, a mixture of (+) and (−) enantiomeric or (+) racemic hexahydro-trans-4a,9b-pyridoindole derivatives of formula I

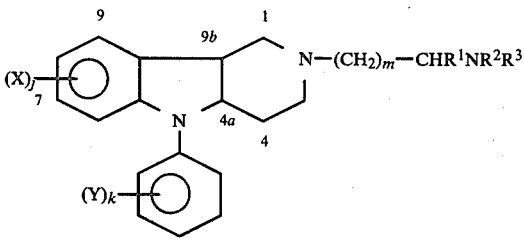

and the pharmacologically acceptable salts thereof.

The optically pure (−) enantiomeric derivatives of formula I have considerably less neuroleptic activity than the corresponding (+) enantiomers or racemic mixtures. Consequently, the pure (−) enantiomers are excluded from the present invention but their mixture with varying amounts of the (+) enantiomers are included.

The variable substituents of formula I are defined as follows:

j and k independently are 1 or 2;

m is 1 to 8;

X and Y are independently selected from H, F, Cl, Br, $OCH_3$, $CH_3$ or $CH_2CH_3$;

$R^1$ is H, alkyl of 1 to 5 carbons, Ph or the mono or disubstituted form of Ph, the mono or disubstituent being F, Cl, Br, $OCH_3$, $CH_3$ or $CH_2CH_3$;

$R^2$ is H, alkyl of 1 to 5 carbons, Ph, $CH_2Ph$ or the mono or disubstituted form of Ph or $CH_2Ph$, the mono or disubstituent being F, Cl, Br, $OCH_3$, $CH_3$ or $CH_2CH_3$;

and $R^3$ is H, alkyl of 1 to 5 carbons, Ph, $CH_2Ph$, alkanoyl of 1 to 8 carbons, alkoxycarbonyl of 2 to 8 carbons, benzoyl, phenylacetyl, alkylsulfonyl of 1 to 8 carbons, phenylsulfonyl or the mono or disubstituted form of Ph, $CH_2Ph$, benzoyl, phenylacetyl, or phenylsulfonyl, the mono or disubstituent being F, Cl, Br, $OCH_3$, $-OCH_2O-$, $CH_3$ or $CH_2CH_3$.

Several types of derivatives are preferred because they exhibit exceptional neuroleptic activity. These include the derivatives wherein $CHR^1NR^2R^3$ is $CH_2NHCOCH_3$, the derivatives wherein $CHR^1NR^2R^3$ is $CH_2NHCOPh$ or the mono or disubstituted form thereof and the derivatives wherein j and k are both 1, X is F at the 8 position and Y is para or ortho F.

Preferred embodiments include the following derivatives:

(+) or (±) 2-(N-acetyl-1'-amino-n-but-4'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 3, $CHR^1NR^2R^3$ is $CH_2NHCOCH_3$, X is 8-F and Y is para-F;

(+) or (±) 2-(N-acetyl-1'-amino-n-pent-5'-yl)-5-(p-fluorophenyl)-8-fluoro-2,3,4,4a,5,9b-hexahydro-trans-4a,9b-(H)-pyrido[4,3-b]indole of (+) enantiomeric or racemic formula I wherein j and k are both 1, m is 4, $CHR^1NR^2R^3$ is $CH_2NHCOCH_3$, X is 8-F and Y is para-F;

(+) or (±) 2-(N-acetyl)-1'-amino-n-hex-6'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 5, $CHR^1NR^2R^3$ is $CH_2NHCOCH_3$, X is 8-F and Y is para-F;

(+) or (±) 2-(N-acetyl-1'-amino-n-hept-7'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 6, $CHR^1NR^2R^3$ is $CH_2NHCOCH_3$, X is 8-F and Y is para-F;

(+) or (±) 2-(N-acetyl-1'-amino-n-oct-8'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 7, $CHR^1NR^2R^3$ is $CH_2NHCOCH_3$, X is 8-F and Y is para-F.

(+) or (±) 2-(N-acetyl-1'-amino-n-non-9'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 8, $CHR^1NR^2R^3$ is $CH_2NHCOCH_3$, X is 8-F and Y is para-F.

(+) or (±) 2-(N-benzoyl-1'-amino-n-but-4'-yl)-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 3, $CHR^1NR^2R^3$ is $CH_2NHCOPh$, X is 8-F and Y is para-F;

(+) or (±) 2-[N-(o-methoxybenzoyl)-1'-amino-n-but-4'-yl]-5-(p-fluorophenyl)-8-fluoro-2,3,4,4a,5,9b-hexahydro-trans-4a,9b-1(H)-pyrido[4,3-b]indole of (+) enantiomeric or racemic formula I wherein j and k are both 1, m is 3, CHR¹NR²R³ is CH₂NHCOC₆H₄OCH₃(o), X is 8-F and Y is para-F;

(+) or (±) 2-(N-ethoxycarbonyl-1'-amino-n-but-4'-yl)-5-(p-fluorophenyl)-8-fluoro-2,3,4,4a,5,9a-hexahydro-trans-4a,9b-1(H)-pyrido[4,3-b]indole of (+) enantiomeric or racemic formula I wherein j and k are both 1, m is 3, CHR¹NR²R³ is CH₂NHCOOC₂H₅, X is 8-F and Y is para-F;

(+) or (±) 2-(N-acetyl-1'-amino-n-but-4'-yl)-5-phenyl-2,3,4,4a,9b-hexahydro-trans-4a,9b-1(H)-pyrido[4,3-b]indole of (+) enantiomeric or racemic formula I wherein j and k are both 1, m is 3, CHR¹NR²R³ is CH₂NHCOCH₃ and X and F are both hydrogen.

The invention also includes pharmaceutical preparations of pharmaceutically acceptable carriers and derivatives of formula I which can be used as neuroleptic agents as well as a method of treating psychotic disorders of a patient by the administration of an efficacious amount of a derivative of formula I to the patient.

DETAILED DESCRIPTION

For the purposes of this discussion, the instant pyrido[4,3-b]indole nucleus

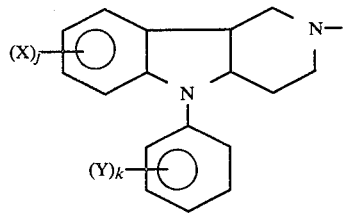

will be represented by

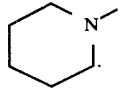

Accordingly, derivatives of formula I are represented by

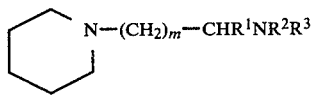

and the starting material pyrido[4,3-b]indole of formula II

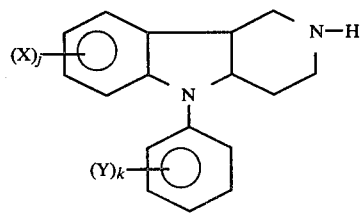

is represented by

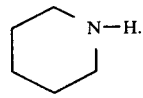

The derivatives may be synthesized by first coupling the known starting material pyrido[4,3-b]-indoles of formula II with the side chain synthon of formula IIIa or IIIb as described in Scheme A or with the acid reagent of formula IIIc as depicted in Scheme B and then by modifying the side chains of these coupling products.

In Scheme A and the discussion about it, the substituents X, Y, Z and m of the formulas are as defined above, Hal is chloro, bromo, p-toluenesulfonyl or methanesulfonyl, R¹ and R² are other than phenyl or mono or disubstituted phenyl and R⁴ is alkyl of 1 to 5 carbons, Ph or mono or disubstituted phenyl, the mono or disubstituent being F, Cl, Br, OCH₃, CH₃ or CH₂CH₃.

SCHEME A

Preparation of Hexahydro-trans-pyridoindole Derivatives of Formula I

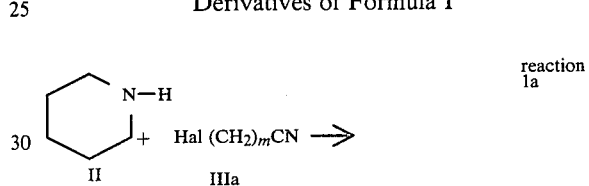

reaction 1a

Nitrile Intermediate.

reaction 1b

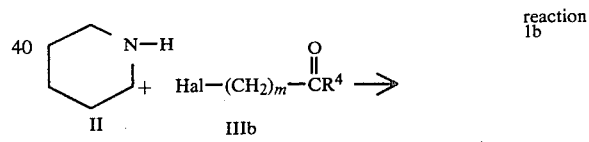

Ketone Intermediate

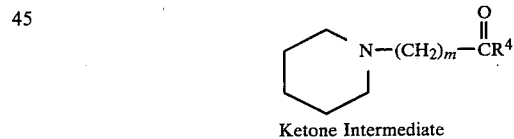

reaction 2

Oxime Intermediate

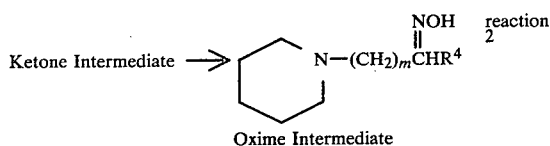

reaction 3

I (R², R³ = H)

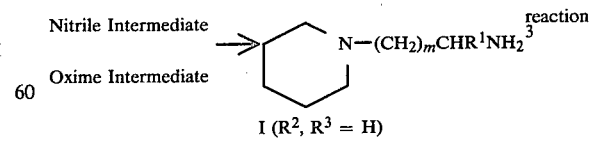

reaction 4a,b or c

I (R², R³ = H)

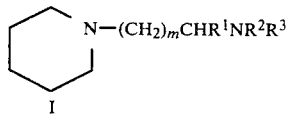

I

Reaction 4a is acylation or sulfonylation. $R^2$ is H and $R^3$ is an acyl or sulfonyl group.

Reaction 4b is alkylation then acylation or sulfonylation. $R^2$ is alkyl, benzyl or mono or disubstituted benzyl and $R^3$ is an acyl or sulfonyl group.

Reaction 4c is dialkylation. $R^2$ and $R^3$ are alkyl, benzyl or mono or disubstituted benzyl.

Preparation of a derivative of formula I wherein $R^2$ or $R^3$ is phenyl or mono or disubstituted phenyl is given in Scheme B.

Composite Reaction 1 (1a and 1b) is the coupling of the side chain synthons IIIa and IIIb and the pyridoindole nucleus and is well known in the art. The product of the reaction is the nitrile intermediate (1a) or ketone intermediate (1b) which must be further modified to produce a derivative of formula I. Reactions 2, 3 and 4 illustrate this conversion and are also well known.

Both reaction 1a and reaction 1b may be conducted by reacting at ambient to reflux temperature about an equi-molar amount of the starting material pyridoindole of formula II and the side chain synthon of formula IIIa or IIIb in an inert polar solvent such as methanol, ethanol, tetrahydrofuran, glyme, lower alkyl ketone, dimethylformamide or dimethylsulfoxide containing at least an equivalent amount of neutralizing agent such as sodium bicarbonate, pyridine or triethylamine and allowing the reaction to proceed until it is substantially complete. The product of the reaction, which will be the nitrile intermediate from reaction 1a or the ketone intermediate from reaction 1b, may be purified using standard techniques such as extraction, crystallization, chromatography or any combination thereof.

Reaction 2 is the conversion of the ketone intermediate to the oxime intermediate. It may be conducted by reacting the ketone with hydroxylamine in ether, tetrahydrofuran, ethanol, methanol or other similar solvent. The oxime intermediate may be purified using standard techniques such as extraction, crystallization, chromatography or any combination thereof.

Reaction 3 is the reduction of the nitrile or oxime intermediate to a derivative of formula I wherein $CHR^1NR^2R^3$ is a primary amine, $CHR^1NH_2$. It may be accomplished using known reagents such as lithium aluminum hydride in ether or tetrahydrofuran or hydrogen over palladium on charcoal or other similar catalyst in methanol, ethanol or ethyl acetate.

The primary amine derivative may be converted to a derivative of formula I wherein $R^2$ or $R^3$ is other than hydrogen by use of composite reaction 4 (reaction 4a, 4b or 4c given below respectively).

To prepare a derivative of formula I wherein $R^2$ is hydrogen and $R^3$ is an acyl or sulfonyl group, i.e., alkanoyl, alkoxycarbonyl, benzoyl, phenylacetyl, alkylsulfonyl, phenylsulfonyl or the mono or disubstituted form of benzoyl, phenylacetyl or phenylsulfonyl, the primary amine derivative of formula I is acylated or sulfonated using Schotten-Baumann or diimide (DCC) "acylation" conditions. The Schotten-Baumann "acylation" may be conducted by reacting the primary amine derivative with the appropriate aryl or sulfonyl halide (Cl, Br) in an inert solvent such as methylenechloride, lower alkyl ketone, dimethylformamide or dimethylsulfoxide containing a neutralizing agent such as sodium bicarbonate, pyridine or triethylamine. The dicyclohexyl carbodiimide (DCC) "acylation" may be conducted by reacting the primary amine derivative with the carboxylic or sulfonic acid corresponding to the desired acyl or sulfonyl group and with DCC in a solvent such as methylene chloride, chloroform, diethyl ether or tetrahydrofuran. The product from either method may be purified using standard techniques such as extraction, crystallization, column chromatography or any combination thereof.

To prepare a derivative of formula I wherein $R^2$ is alkyl, benzyl or mono or disubstituted benzyl and $R^3$ is an acyl or sulfonyl group, the primary amine derivative of formula I is first alkylated then acylated or sulfonated. The alkyl, benzyl or mono or disubstituted benzyl intermediate may be prepared using the appropriate alkyl, benzyl or mono or disubstituted benzyl chloride, bromide, iodide or sulfate. The "acylation" reaction is conducted as described above.

A derivative of formula I wherein $R^2$ and $R^3$ are alkyl, benzyl or mono or disubstituted benzyl is prepared by dialkylating or sequentially monoalkylating the primary amine derivative of formula I. For example to prepare a derivative wherein $R^2$ and $R^3$ are equal, at least two equivalents of the alkyl, benzyl or mono or disubstituted benzyl chloride, bromide, iodide or sulfate are added to the primary amine derivative in an inert solvent such as methanol, ethanol, glyme or tetrahydrofuran containing a neutralizing agent such as sodium bicarbonate, pyridine or triethyl amine. The dialkylated derivative is purified using standard techniques such as extraction, crystallization, column chromatography or a combination thereof. To prepare a derivative wherein $R^2$ and $R^3$ are not equal, the same procedure is used except that the monoadduct is first prepared which is alkylated with the second desired alkyl, benzyl or mono or disubstituted benzyl chloride, bromide, iodide or sulfate. Of course, a monoadduct derivative of formula I wherein $R^2$ is alkyl, benzyl or mono or disubstituted benzyl and $R^3$ is H, is prepared by the same procedure using an appropriate ratio of reactants.

Scheme B presents another route for the preparation of some derivatives wherein $R^2$ and $R^3$ are hydrogen, alkyl, phenyl, benzyl or mono or disubstituted phenyl or benzyl. In Scheme B and the discussion about it, the substitutents X, Y, Hal, j, k and m are as previously defined; $R^1$ is hydrogen and $R^2$ and $R^3$ have the restricted definitions just set forth.

SCHEME B

Another Route to Some Hexahydro-trans-pyridoindole Derivatives

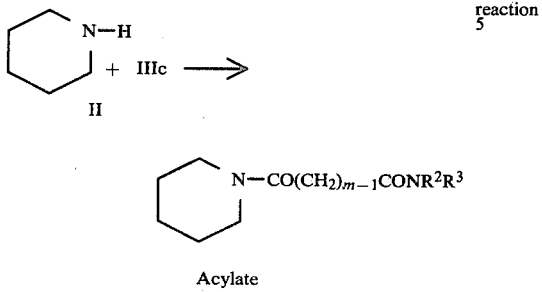

Acylate

-continued

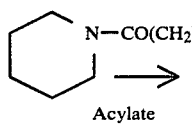

Acylate

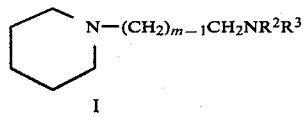

I

Reaction 5 is the coupling of the starting material pyridoindole of formula II and the acid reagent of formula IIIc, $HO_2C(CH_2)_{m-1}CONR^2R^3$ to produce the acylate. The coupling conditions are well known. The starting material pyridoindole is treated with the acid reagent in the presence of dicyclohexylcarbodiimide (DCC conditions) in a solvent such as chloroform, methylene chloride, diethyl ether or tetrahydrofuran until the coupling is substantially complete. Alternatively the starting material pyridoindole may be treated with the acyl halide corresponding to the acid reagent under Schotten-Baumann conditions described above. The acylate is purified using standard techniques such as extraction, crystallization, column chromatography or any combination thereof.

Reaction 6, is the conversion of the acylate to the desired derivative of formula I. Use of a reducing agent such as lithium aluminum hydride in an inert solvent such as ether, tetrahydrofuran or glyme will reduce the both amide functions at the 2 position and $CONR^2R^3$ to the desired amine functions. After quenching the remaining hydride with a reagent such as water, alcohol or a hydrated inorganic salt the derivative may be purified using standard techniques such as extraction, crystallization, column chromatography or any combination thereof.

The acid reagent IIIc may be prepared by coupling the appropriate amine, $HNR^2R^3$, with the appropriate half acid, half ester $HO_2C(CH_2)_{m-1}CO_2CH_3$ under DCC or Schotten-Baumann conditions followed by hydrolysis of the ester function of the resulting half ester, half amide.

The optically active or racemic derivatives may be prepared using the corresponding optically active or racemic starting material pyridoindoles. The racemic derivatives may also be resolved using methods known in the art for resolving racemic amines, see Fieser et al. "Reagents for Organic Synthesis" Wiley and Sons, Inc., New York (1967), Vol. 1, page 977 and references cited therein. For example, formation of the amine salt using D-pyroglutamic acid produces the diastereomers which may then be separated by fractional crystallization. The resolved (+) enantiomer can be obtained by basifying the resolved salt.

The pharmacologically acceptable salts of the derivatives may be prepared by reaction with about an equivalent of an organic or mineral acid in either aqueous or nonaqueous solution. Such acids include hydrochloric, hydrobromic, hydroiodic, sulfuric, phosphoric, acetic, lactic, citric, tartaric, succinic, maleic and gluconic acids. The salt may be isolated by removal of the solvent in vacuo or in an appropriate case, by precipitation.

The derivatives are useful as neuroleptic agents in the treatment of mental disorders and illnesses including schizophrenia, psychoses and neuroses. Symptoms requiring such treatment include anxiety, aggression, agitation, depression, hallucinations, tension and emotional or social withdrawal. In general, the derivatives exhibit major tranquilizing activity but have fewer side effects than the drugs presently in use.

The derivatives can be formulated in a variety of pharmaceutical preparations which contain the derivative alone or in combination with pharmaceutical carriers such as inert solid diluents, aqueous solutions or various non-toxic, organic solvents and in dosage forms such as gelatin capsules, tablets, powders, lozenges, syrups, injectable solutions and the like. Such carriers include water, ethanol, gelatins, lactose, starches, vegetable oils, petroleum jelly, gums, glycols, talc, benzoyl alcohols, and other known carriers for medicaments. If desired, these pharmaceutical preparations may contain additional material such as preserving agents, wetting agents, stabilizing agents, lubricating agents, absorption agents, buffering agents and isotonic agents.

The derivatives may be administered to a patient in need of treatment by a variety of conventional routes of administration such as oral, intravenous, intramuscular, subcutaneous or intraperitoneal. In general, small doses will be administered initially with a gradual increase in the dose until the optimum level is determined. However, as with any drug the particular dose, formulation and route of administration will vary with the age, weight and response of the particular patient and will depend upon the judgment of his attending physician.

In the usual course of treatment a dose of a derivative of approximately 0.1 mg per day to 100 mg per day will provide effective treatment for the human patient. When the derivative has a prolonged effect, the dose can be administered every other day or in 1 or 2 divided doses per week.

The tranquilizing activity of the derivatives may be determined using the well known standard procedure-antagonism of amphetamine-induced symptoms in rats. This method has excellent correlation with human efficacy and is taught by A. Weissman, et al., *J. Pharmacol. Exp. Ther.* 151, 339 (1966) and by Quinton, et al., *Nature,* 200, 178, (1963). As illustrated below this method shows that the derivatives have excellent tranquilizing activity compared to the standard test drug, chlorpromazine.

So called "intrinsic" tranquilizing activity of the derivatives may be determined using the method of Leysen et. al., *Biochem, Pharmacol.,* 27, 307 (1978). The ability of the drug to inhibit $^3H$-spiroperidol binding to dopamine receptors is measured and the results correlate with the relative pharmacological potencies of drugs affecting behavior mediated by dopamine receptors [Burt, et al., *Molecular Pharmacol.,* 12, 800 (1976)]. As given below, this intrinsic method shows that the derivatives have excellent neuroleptic activity.

The present invention is illustrated by the following examples. It will be understood, however, that the invention is not limited to the specific details of these examples.

EXAMPLE 1

(±)2-(1'-cyano-n-prop-3'-yl)-5-p-fluorophenyl-8-fluoro-2,3,4,4a,5,9b-hexahydro-trans-4a,9b-1(H)-pyrido[4,3-b]indole (nitrile intermediate 1)

A stirred suspension of 8-fluoro-5-(p-fluorophenyl)2,3,4,4a,-5,9b-hexahydro-trans-4a,9b-1(H)- pyrido[4,3-b]indole (starting material pyridoindole sm) (1 g, 3.49 mM), gamma-bromo-butyronitrile, (0.723 g, 4.88 mM), anhydrous sodium carbonate, (2.1 g, 20.9 mM), potassium iodide, (0.289 g, 1.74 mM), in methyisobutylketone, (40 ml), under nitrogen was refluxed for 16 hours. The reaction mixture was cooled to room temperature and evaporated in vacuo to dryness. The resulting white solid was partitioned between water (40 ml) and chloroform (50 ml). The phases were separated and the aqueous phase extracted with chloroform (50 ml). The organic layers were combined, dried (MgSO$_4$), and evaporated in vacuo to give a pale yellow oil. Treatment of the oil with hydrogen chloride gas in acetone (40 ml), gave upon filtration and washing with acetone (10 ml) 0.813 g, (60% yield) of the above titled nitrile intermediate (1) as a white solid, mp 245°–249° C. (HCl salt).

CHN analysis calc'd for $C_{21}H_{21}N_3F_2.HCl$; C-64.67, H-5.42, N-10.77. Found: C-64.38, H-5.71; N-10.71.

EXAMPLE 2

(±)2-(1'-amino-n-but-4'-yl)-5-(p-fluorophenyl)-8-fluoro-2,3,4,4a,5,9b-hexahydro-trans-4a,9b-1(H)-pyrido[4,3-b]indole (Derivative 2)

To a stirred suspension of lithium aluminum hydride (0.167 g, 4.4 mM) in diethyl ether (35 ml), under nitrogen, was added the nitrile intermediate (1) of Example 1 (0.781 g, 2.0 mM) at a rate sufficient to maintain the reaction temperature 28°–30° C. (15 min). After stirring for 4 hr at ambient temperature, Glaubers Salt (Na$_2$SO$_4$.10H$_2$O) (1.2 g, 4 mM) was added portion wise over a 10 min peroid. The white solid was filtered and washed with diethyl ether (10 ml) and the filtrate evaporated in vacuo to give a pale yellow oil. Treatment of the oil with hydrogen chloride in ether (35 ml), gave upon filtration and washing with ether (20 ml), 0.498 g, (64% yield) of the above titled Derivative (2) as a white solid mp 224°–227° C. (HCl salt).

CHN analysis: calc'd for $C_{21}H_{25}N_3F_2.2.5H_2O.HCl$; C-53.28, H-6.38; N-8.87. Found: C-52.98, H-5.94, N-8.66.

EXAMPLE 3

(±)2-(N-acetyl-1'-amino-n-but-4'-yl)-5-(p-fluorophenyl)-8-fluoro-2,3,4,4a,5,9b-hexahydro-trans-4a,9b-1(H)-pyrido[4,3-b]indole (Derivative 3)

To a stirred solution of the Derivative (2) of Example 2 (0.315 g, 0.803 mM), triethylamine (0.44 ml, 3.2 mM), and methylene chloride (10 ml), under nitrogen at 2° (ice bath), was added acetyl chloride (0.063 ml 8.8 mM) in 5 ml methylene chloride at a rate sufficient to maintain the reaction temperature 2°–5° C. After stirring at ambient temperature for 2 hours the reaction mixture was poured onto saturated sodium bicarbonate solution (30 ml). The phases were separated and the aqueous phase extracted with methylene chloride (30 ml). The organic layers were combined, dried (MgSO$_4$), and evaporated in vacuo to give a pale yellow oil. Treatment of the oil with hydrogen chloride in isopropanol (5 ml) gave upon filtration 0.230 g, (65% yield) of the above titled Derivative (3) as a white solid, mp 243°–245° C. (HCl salt).

CHN analysis: calc'd for $C_{23}H_{27}ON_3F_2.HCl$; C-63.36, H-6.47, N-9.63. Found; C-63.25, H-6.48, N-9.73.

EXAMPLE 4

(±)2-[N-phenylsuccinamoyl)-5-(p-fluorophenyl)-8-fluoro-2,3,4,4a,5,9b-hexahydro-trans-4a,9b-1(H)pyrido[4,3-b]indole (Acylate 4)

To a stirred solution of 4a,9b-trans-8-fluoro-5-(p-fluorophenyl)-2,3,4,4a,5,9b-hexahydro-trans-4a,9b-1(H)-pyrido[4,3-b]indole (starting material pyridoindole sM) (1 g), N-phenylsuccinamic acid (acid reagent AR4) (9 g) and methylene chloride (20 ml), under nitrogen at 2° C. (ice bath) is added dicyclohexylcarbodiimide (1 g). The reaction mixture is allowed to stir at 2°–4° C. for about 30 minutes then at ambient temperature for 2 hours. The reaction mixture is then cooled to 2° C. (ice bath) and the white solid dicyclohexyl urea may be filtered and washed with cold methylene chloride (5 ml). The filtrate is evaporated in vacuo and the residue may be purified by crystallization or chromatographic techniques to yield the above titled Acylate (4).

EXAMPLE 5

(±)2-(N-phenyl-1'-amino-n-but-4'-yl)-5-(p-fluorophenyl)-8-fluoro-2,3,4,4a,5,9b-hexahydro-trans-4a,9b-1(H)pyrido[4,3-b]indole (Derivative 5)

To a stirred suspension of lithium aluminum hydride (0.2 g) in diethyl ether (40 ml), under nitrogen is added Acylate (4) of Example 4 (1 g) at a rate sufficient to maintain the reaction temperature at 28°–30° C. After stirring for about 2 hours at ambient temperature, Glaubers Salt (Na$_2$SO$_4$.10H$_2$O) (2 g) may be added portionwise. The white solid may be filtered and washed with diethyl ether. The filtrate is evaporated in vacuo and the residue purified by crystallization or chromatographic techniques to yield the above titled Derivative (5).

EXAMPLES 6 THROUGH 17

The following Derivatives were prepared by following the procedures of Examples 1 through 5 and by substituting the appropriate side chain synthon or acid reagent for side chain synthon (SCSl) of Example 1 or acid reagent (AR4) of Example 4. Other Derivatives may be prepared by substituting the appropriate starting material pyridoindole of formula II and by substituting the appropriate side chain synthon of formula IIIa or b or appropriate acid reagent of formula IIIc for the corresponding material in Examples 1 through 5.

The pyridoindole nucleus used for almost all the synthesized derivatives is 5-(p-fluorophenyl)-8-fluoro-2,3,4,4a,5,9b-hexahydro-trans-4a,9b-1(H)-pyrido[4,3-b]indole. Consequently unless otherwise indicated, the name of the Derivative of each of the following examples is given as the 2-position substituent (the side chain) and it will be understood that the above pyridoindole nucleus is part of each name. For instance, the complete name of the Derivative of Example 6 is 2-(N-acetyl-2-aminoethyl)-5-(p-fluorophenyl)-8-fluoro-2,3,4,4a,5,9b-hexahydro-trans-4a,9b-1(H)-pyrido[4,3-b]indole.

| Example | Name | mp °C. | Empirical formula | analysis C | 1. calc'ed 2. found H | N |
| --- | --- | --- | --- | --- | --- | --- |
| 6 | (±) 2-(N—acetyl-2-amino-ethyl) hydrochloride salt | 229–33 | $C_{21}H_{23}ON_3F_2$ $\cdot H_2O\cdot HCl$ | 1. 59.24 2. 59.34 | 6.15 5.78 | 9.86 9.97 |
| 7 | (±) 2-(N—acetyl-1'-amino-n-prop-3-yl) hydrochloride salt | 224–7 | $C_{22}H_{25}ON_3F_2$ $\cdot\tfrac{1}{2}0\,H_2O\cdot HCl$ | 1. 61.31 2. 61.50 | 6.08 6.32 | 9.75 9.30 |
| 8 | (±) 2-(N—acetyl-1'-amine-n-pent-5'-yl) hydrochloride salt | 237–40 | $C_{24}H_{29}ON_3F_2$ $\cdot H_2O\cdot HCl$ | 1. 61.59 2. 61.82 | 6.89 6.40 | 8.97 8.80 |
| 9 | (±) 2-(N—acetyl-1'-amino-n hex-6'-yl) hydrochloride salt | 204–8 | $C_{25}H_{31}ON_3F_2$ $\cdot 2H_2O\cdot HCl$ | 1. 60.05 2. 60.13 | 7.00 6.58 | 8.40 8.33 |
| 10 | (±) 2-(N—acetyl-1'-amino-n-hept-7'-yl) hydrochloride salt | 217–21 | $C_{26}H_{33}ON_3F_2$ $\cdot 1\tfrac{1}{4}H_2O\cdot HCl$ | 1. 62.39 2. 62.41 | 7.24 7.09 | 8.39 8.34 |
| 11 | (+) enantiomer of 2-(N—acetyl-1-'-amino-n-but-4-yl) (Derivative 3) hydrochloride salt | 253–6 | same as Derivative (3) | | | |
| 12 | (−) enantiomer of 2-(N—acetyl-1'-amino-n-but-4'-yl) (Derivative 3) hydrochloride salt | 255–8 | Same as Derivative (3) | | | |
| 13 | (±) 2-(N—benzoyl-1'-amino-n-but-4'-yl) hydrochloride salt | 259–62 | $C_{28}H_{29}ON_3F_2$ $\cdot 2H_2O\cdot HCl$ | 1. 62.97 2. 63.11 | 6.22 6.00 | 7.86 8.03 |
| 14 | (±) 2-(N—ethoxycarbonyl-1'-amino-n-but-4'-yl) hydrochloride salt | amorphous | $C_{24}H_{29}O_2N_3F_2$ $\cdot\tfrac{1}{2}H_2O\cdot HCl$ | 1. 60.68 2. 60.46 | 6.57 6.49 | 8.87 8.79 |
| 15 | (±) 2-[N—(o-methoxybenzoyl)-1'-amino-n-but-4'-yl] hydrochloride salt | foam | $C_{29}H_{31}O_2N_3F_2$ $\cdot H_2O\cdot HCl$ | 1. 63.78 2. 63.50 | 6.27 6.13 | 7.69 7.55 |
| 16 | (±) 2-(N—p-toluenesulfonyl-1'-amino-n-but-4'-yl) hydrochloride salt | amorphous | $C_{28}H_{31}O_2N_3SF_2$ $\cdot\tfrac{1}{2}H_2O\cdot HCl$ | 1. 60.36 2. 60.13 | 5.97 6.00 | 7.54 7.25 |
| 17 | (±) 2-(N—acetyl-1'-amino-n-but-4'-yl)-5-phenyl-2,3,4,-4a,9b-hexahydro-trans-4a,9b-1(H)-pyrido[4,3-b]indole | 238–240 | $C_{23}H_{29}ON_3\cdot HCl$ $\cdot 1\tfrac{1}{4}H_2O$ | 1. 65.38 2. 65.34 | 7.63 7.09 | 9.94 9.86 |

EXAMPLE 18

Antagonism of Amphetamine Symptoms in Rats Test Procedures and Results

The effects of the above examples of Derivatives on prominent amphetamine-induced symptoms were studied in rats by a rating scale modeled after the one reported by Quinton and Halliwell, and Weissman. Rats were placed individually in a covered plastic cage measuring approximately 26 cm.×42 cm×16 cm. After a brief period of acclimation of the cage, the rats in each group, commonly, five animals per dose level, were treated subcutaneously (s.c.) with a selected dose of the Derivative to be tested. They were then treated 1, 5 and 24 hrs. later with d-amphetamine sulfate, 5 mg./kg. intraperitoneally (i.p.). One hour after amphetamine was given, each rat was observed for the characteristic amphetamine behaviour of moving around the cage. On the basis of dose-response data after amphetamine it was possible to determine the effective dose of the compound necessary to antagonize or block the characteristic amphetamine behaviour of cage movement for fifty percent of the rats tested ($ED_{50}$). The time of rating chosen coincides with the peak action of amphetamine which is 60–80 min. after dosing. The results ($ED_{50}$) of tests on the Derivatives of Examples 2, 3, 6–17 and subcutaneously administered chlorpromazine, a comparative drug, are given in Table 1 below.

TABLE 1

Rat Amphetamine Test

| | $ED_{50}$(mg/kg) | | |
| --- | --- | --- | --- |
| Example | 1 hr. | 5 hr. | 24 hr. |
| 2 | 17.7 | 4.5–11.5 | 17.7 |
| 3 | 0.02 | 0.006 | 0.66 |
| 6 | 0.11 | 0.36 | 1 |
| 7 | NT | NT | NT |
| 8 | 0.01 | 0.004 | 0.4 |
| 9 | 0.023 | 0.002 | 0.032 |
| 10 | 0.09 | 0.018 | 0.05 |
| 11 | 0.02 | 0.006 | 0.28 |
| 12 (−) enantiomer | 1 | 1 | 1 |
| 13 | 0.1–0.3 | 0.01–0.03 | 0.3–1 |
| 14 | 0.05 | 0.02 | 0.3 |
| 15 | 0.45 | 0.18 | 1 |
| 16 | 1 | 1 | NT |
| 17 | 1.0–0.1 | 1.0–0.1 | 1.0–0.1 |
| Chlorpromazine | 5.3 | 8.5 | 32 (s.c.) |

NT is not tested.

EXAMPLE 19

Inhibition of $^3$H-Spiroperidol Binding to Dopamine Reactors

Test Procedures and Results

The relative affinity of the derivatives for receptors was studied using $^3$H-spiroperidol (spiperone) as the labeled ligand following the method of Leysen et al. *Biochem Pharmacol,* 27, 307–316 (1978). The procedure was as follows:

Rats (Sprague-Dawley CD males, 250-300 g., Charles River Laboratories, Wilmington, Mass.) were decapitated, and brains were immediately dissected on an ice-cold glass plate to remove corpus striatum (∼100 mg./brain). Tissue was homogenized in 40 volumes (1 g.+40 ml). of ice-cold 50 mM. Tris (tris [hydroxymethyl]aminomethane; (THAM) .HCl buffer pH 7.7. The homogenate was centrifuged twice at 50,000 g. (20,000 rpm) for 10 minutes with rehomogenization of the intermediate pellet in fresh THAM buffer (same volume). The final pellet was gently resuspended in 90 volumes of cold, freshly prepared (<1 week old) stock solution, 50 mM Tris buffer pH 7.6 containing 120 mM NaCl (7.014 g./l.), 5 Mm KCl (0.3728 g/l.), 2 mM $CaCl_2$ (0.222 g./l.), 1 mM $MgCl_2$ (0.204 g./l.), 0.1% ascorbic acid (1 mg./ml.) and 10 micro M pargyline (100 micro 1. stock/100 ml. buffer; stock=15 mg./10 ml. DDW). Ascorbic acid and pargyline were added fresh daily. The tissue suspension was placed in a 37° C. water bath for 5 minutes to insure inactivation of tissue monoamine oxidase and then kept on ice until used. The incubation mixture consisted of 0.02 ml. inhibitor solution (the desired concentration of the derivative to be tested in stock solution). 1.0 ml. tissue homogenate and 0.10 ml label ($^3$H-spiroperidol, New England Nuclear 23.6 Ci/mmole), prepared so as to obtain 0.5 nM in the final incubation medium (usually diluted 2.5 μl. stock to 17 ml. DDW). Tubes were incubated in sequence for 10 minutes at 37° C. in groups of three, after which 0.9 ml. of each incubation tube was filtered through Whatman FG/B filters using a high vacuum pump. Each filter was placed in a scintillation vial, 10 ml. of liquid scintillation fluor was added and each vial was vigorously vortexed for about five seconds. Samples were allowed to stand over night, until filters were translucent, vortexed again and then counted 1.0 minute for radioactivity. Binding was calculated as femtomales ($10^{-15}$ moles) of $^3$H-spiroperidol bound per mg. protein. Controls (vehicle or 1 butaclamol, $10^{-7}$M; 4.4 mg. dissolved in 200 μl. glacial acetic acid, then diluted to 2.0 ml. with DDW for $10^{-4}$M stock solution, kept refrigerated), blank (d-butaclamol, $10^{-7}$M; (4.4 mg./2 ml.) for $10^{-4}$M stock solution, same protocol as l-butaclamol); and inhibitor solutions were run in triplicate. The concentration reducing binding by 50% ($IC_{50}$) was estimated on semi-log paper. Insoluble drugs were dissolved in 50% ethanol (1% ethanol incubation).

**DDW=Double Distilled Water.

The results using the derivatives of Examples 2, 3, 6-17 and subcutaneously administered chlorpromazine are reported below in Table 2 as the nanomolar concentration required to produce 50% inhibition of $^3$H-Spiroperidol binding.

TABLE 2
Inhibition of $^3$H Spiroperidol
Binding to Dopamine Receptors

| Example | $IC_{50}$ (nM) |
|---|---|
| 2 | 24 |
| 3 | 13 |
| 6 | 16 |
| 7 | 10 |
| 8 | 9 |
| 9 | 8 |
| 10 | 9 |
| 11 | 4.7 |
| 12 | 1000 |
| 13 | 19 |
| 14 | 11 |
| 15 | 14 |
| 16 | 27 |
| 17 | 16 |
| Chlorpromazine | 51 (s.c.) |

We claim:

1. A (+) enantiomeric, a mixture of (+) and (−) enantiomeric or (+) racemic hexahydro-trans-4a,9b-1(H)pyridoindole derivative of the formula

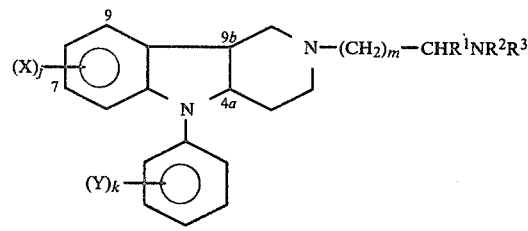

or a pharmacologically acceptable salt thereof, wherein
j and k are independently 1 or 2;
m is 1 to 8;
X and Y are independently H, F, Cl, Br, $OCH_3$, $CH_3$ or $CH_2CH_3$;
$R^1$ is H, alkyl of 1 to 5 carbons, Ph or the mono or disubstituted form of Ph, the mono or disubstituent being F, Cl, Br, $OCH_3$, $CH_3$ or $CH_2CH_3$;
$R^2$ is H, alkyl of 1 to 5 carbons, Ph, $CH_2$Ph or the mono or disubstituted form of Ph or $CH_2$Ph, the mono or disubstituent being F, Cl, Br, $OCH_3$, $CH_3$ or $CH_2CH_3$; and
$R^3$ is alkanoyl of 1 to 8 carbons, alkoxycarbonyl of 2 to 8 carbons, benzoyl, phenylacetyl, alkylsulfonyl of 1 to 8 carbons, phenylsulfonyl or a ring mono or disubstituted form of benzoyl, phenylacetyl, or phenylsulfonyl, the mono or disubstituent being F, Cl, Br, $OCH_3$, $—OCH_2O—$, $CH_3$ or $CH_2CH_3$.

2. A derivative of claim 1 wherein $CHR^1NR^2R^3$ is $CH_2NHCOCH_3$.

3. A derivative of claim 2 wherein j and k are both 1, X is 8-F and Y is para F.

4. The (+) enantiomeric or racemic derivative of claim 3 wherein m is 3.

5. The (+) enantiomeric or racemic derivative of claim 3 wherein m is 4.

6. The (+) enantiomeric or racemic derivative of claim 3 wherein m is 5.

7. The (+) enantiomeric or racemic derivative of claim 3 wherein m is 6.

8. A derivative of claim 1 wherein $CHR^1NR^2R^3$ is $CH_2NHR^3$ and $R^3$ is benzoyl or mono disubstituted benzoyl.

9. The (+) enantiomeric or racemic derivative of claim 8 wherein j and k are both 1, X is 8-F, Y is para-F, m is 3 and $R^3$ is benzoyl.

10. The (+) enantiomeric or racemic derivative of claim 8 wherein j and k are both 1, X is 8-F, Y is para-F, m is 3 and $R^3$ is o-methoxybenzoyl.

11. A derivative of claim 1 wherein j and k are both 1, X is 8-F and Y is para or ortho-F.

12. The (+) enantiomeric or racemic derivative of claim 11 wherein m is 3, Y is para-F and $CHR^1NR^2R^3$ is $CH_2NHCOOC_2H_5$.

13. The (+) enantiomeric or racemic derivative of claim 1 wherein m is 3, X and Y are both H and $CHR^1NR^2R^3$ is $CH_2NHCOCH_3$.

14. A pharmaceutical composition for use as a neuroleptic agent which comprises an effective amount of a derivative of claim 1 together with an inert pharmaceutical adjuvant, diluent or carrier.

15. A method of treating schizophrenic psychoses and neuroses in a patient requiring major tranquilization which comprises administering to the patient by oral, intravenous, intramuscular, subcutaneous or intraperitoneal route an effective amount of a derivative of claim 1 or of a composition of claim 14.

* * * * *